United States Patent [19]
Cassford et al.

[11] Patent Number: 5,542,911
[45] Date of Patent: Aug. 6, 1996

[54] ORTHOPEDIC BRACE HAVING A SYSTEM OF ALTERNATELY INFLATABLE OR DEFLATABLE PNEUMATIC PADS FOR ADJUSTABLE FITTING OF THE BRACE TO THE BODY

[75] Inventors: Keith L. Cassford, San Diego; Richard E. Gildersleeve, Escondido; Charles A. Bastyr, San Diego, all of Calif.

[73] Assignee: Smith & Nephew Donjoy Inc., Carlsbad, Calif.

[21] Appl. No.: 399,085

[22] Filed: Mar. 8, 1995

Related U.S. Application Data

[63] Continuation of Ser. No. 104,184, Aug. 10, 1993, Pat. No. 5,415,625, which is a continuation-in-part of Ser. No. 907,160, Jul. 1, 1992, Pat. No. 5,316,517.

[51] Int. Cl.⁶ ..................................................... A61F 5/00
[52] U.S. Cl. ................................. 602/26; 602/13; 602/16
[58] Field of Search ................................. 602/13, 16, 26, 602/5, 14, 20, 23, 25; 128/878, 882; 607/108, 112, 114

[56] References Cited

U.S. PATENT DOCUMENTS

| | | | |
|---|---|---|---|
| Re. 34,661 | 7/1994 | Grim | 602/13 X |
| 4,567,887 | 2/1986 | Couch, Jr. | 602/13 X |
| 4,682,588 | 7/1987 | Curlee | 602/13 |
| 4,872,448 | 10/1989 | Johnson, Jr. | 602/13 X |
| 5,152,740 | 10/1992 | Harkensee et al. | 602/13 |
| 5,288,286 | 2/1994 | Davis et al. | 602/13 X |
| 5,316,547 | 5/1994 | Gildersleeve | 602/13 X |
| 5,360,394 | 11/1994 | Christensen | 602/13 X |
| 5,415,625 | 5/1995 | Cassford et al. | 602/13 X |

*Primary Examiner*—Linda C. Dvorak
*Attorney, Agent, or Firm*—Brown, Martin, Haller & McClain

[57] ABSTRACT

A hinged knee brace has a system of inflatable pads mounted thereon to adjustably provide secure and comfortable support for the brace against the leg. Each pad is a pneumatic bladder having a valve enabling selective inflation or deflation of the bladder with a fluid to systematically adjust the fit of the brace to the leg in accordance with the needs of the user.

5 Claims, 2 Drawing Sheets

5,542,911

ORTHOPEDIC BRACE HAVING A SYSTEM OF ALTERNATELY INFLATABLE OR DEFLATABLE PNEUMATIC PADS FOR ADJUSTABLE FITTING OF THE BRACE TO THE BODY

This application is a continuation of co-pending patent application Ser. No. 08/104,184, filed Aug. 10, 1993, now issued as U.S. Pat. No. 5,415,625, which is a continuation-in-part of Ser. No. 07/907,160, filed Jul. 1, 1992, now issued as U.S. Pat. No. 5,316,547.

TECHNICAL FIELD

The present invention relates generally to an orthopedic brace, and particularly to an orthopedic brace having a pad mounted thereon for supporting the brace against the body of a user. More particularly, though not exclusively, the present invention relates to an orthopedic brace having a system of pneumatic pads mounted thereon that support the brace against the body in close fit therewith by selectively inflating or deflating the pads in correspondence to the body.

BACKGROUND OF THE INVENTION

Orthopedic braces are commonly employed on the body of a user to stabilize a skeletal joint that has been weakened by injury or other infirmity. The braces characteristically have either rigid or elastic structural components supporting the joint. Typically, the structural components of rigid braces are dynamically linked together by hinges enabling controlled movement of the joint during rehabilitative therapy or routine user activity. Such braces are positioned on the body so that the hinges traverse the joint being stabilized, while the rigid components are secured to the body along a plurality of engagement faces above and below, as well as adjacent to the joint. Substantially solid elastomeric pads or fluid-filled pneumatic pads are often positioned on the brace between the body and the rigid support components to enhance the fit of the brace with the body and to cushion the body of the user from the engagement faces.

Despite the placement of pads on rigid braces, the user frequently experiences discomfort from painful point loads while wearing a closely-fitted padded brace because of the high forces the brace applies to the body across the engagement faces during routine activity or rehabilitative therapy. Such discomfort is particularly acute where the pad does not possess proper compression characteristics or the brace is not properly sized and configured in conformance with the structure of the brace and the contours of the body. It has also been found that body tissue undergoes transient changes, such as swelling or shrinkage, during routine or rehabilitative physical activity for which pads employed in rigid braces are not configured and consequently to which such pads do not readily adjust.

U.S. Pat. No. 4,201,203 discloses an elastic knee brace having an open-loop, elastomeric pad conformable to the patella. U.S. Pat. No. 4,777,946 similarly discloses an elastic knee brace having a closed-loop, elastomeric pad conformable to the patella. U.S. Pat. No. 4,378,009 and U.S. Pat. No. 4,938,207 both disclose elastic knee braces having inflatable pneumatic pads conformable to the patella. Nevertheless, corresponding body-conforming pneumatic pads are not found in rigid orthopedic braces.

U.S. Pat. No. 5,125,400 discloses a rigid orthopedic brace having inflatable pneumatic pads positioned between the ankle of the user and the rigid support components of the brace. U.S. Pat. No. 5,107,823 discloses a thigh guard having an inflatable pneumatic pad positioned between the thigh and a rigid protective shell. In both instances, however, the pads are not significantly configured in conformance with the corresponding body contours.

Some rigid orthopedic braces have specifically addressed the problem of closely fitting the rigid brace with the knee or elbow while simultaneously cushioning the body from the brace. French patent publication FR 2627-381-A discloses a rigid brace having a pair of rounded, incompressible fluid-filled pads positioned on the brace to abut the knee or elbow condyles. U.S. Pat. No. 3,581,741 discloses a rigid brace having a doughnut-shaped solid elastomeric pad positioned against the medial meniscus of the knee in association with an adjacent inflatable pneumatic thigh pad. Yet, the prior art does not disclose pneumatic pads configured in substantial conformance with the contours of the user's body.

Accordingly, it is an object of the present invention to provide an orthopedic brace that can be secured to the body of a user with both a high degree of stable support and a high degree of user comfort. It is further an object of the present invention to provide an orthopedic brace employing a plurality of pads that systematically stabilizes the brace against the body of the user by dynamically conforming to the contours of the body and the structure of the brace, while cushioning the contours from the rigid structural components of the brace.

It is another object of the present invention to provide an off-the-shelf orthopedic brace that can be adapted to fit the body contours of any number of users. It is another object of the present invention to provide a custom orthopedic brace that is readily configured to the body contours of a specific individual user. It is still another object of the present invention to provide an orthopedic brace having a fit that can be instantaneously adapted to the requirements of different activities by the user. It is a further object of the present invention to provide an orthopedic brace having a fit that can be instantaneously adjusted to transient conditions of the body such as localized tissue swelling or shrinkage.

SUMMARY OF THE INVENTION

The present invention is an orthopedic brace having a system of inflatable pads mounted thereon that adjustably provides a secure and comfortable fit of the brace against the body of a user. Each pad comprises a pneumatic bladder penetrated by a valve enabling selective fluid communication between the interior and exterior of the bladder. Thus, the bladders are selectively inflated or deflated with a fluid to systematically adjust the size, and correspondingly the fit, of the brace to the body in accordance with the needs of the user.

The present invention is specifically applicable to a hinged knee brace mountable on the leg of a user to stabilize the knee joint by restricting motion thereof. The brace comprises a frame made up of substantially rigid components including upper and lower leg cuffs and a hinge. The upper leg cuff is engagable with the upper leg above the knee joint and the lower leg cuff is engagable with the lower leg below the knee joint. The cuffs are rotatably connected across the hinge which is positionable at the knee joint to pivot in correspondence with flexion and extension of the knee joint as permitted by the brace. The hinge comprises a medial pivot member and a lateral pivot member disposed on opposite sides of the knee joint.

Each cuff comprises a medial arm and a lateral arm longitudinally disposed on opposite sides of the leg in substantially parallel alignment. The lateral arms of the upper and lower leg cuffs are attached at their one end to the lateral pivot member of the hinge. The medial arms of the upper and lower leg cuffs are similarly attached at one end to the medial pivot member of the hinge. Each cuff further comprises a cross member circumferentially disposed in an arcuate configuration on the upper or lower leg. The upper cross member is joined to the remaining ends of the upper medial and lateral arms and the lower cross member is similarly joined to the remaining ends of the lower medial and lateral arms with the cross members being substantially perpendicularly aligned relative to the arms.

The inner surface of the hinge and upper and lower leg cuffs define engagement faces of the frame components with the body. Accordingly, the system of inflatable pads is positioned on the engagement faces of the brace between the rigid components and the body of the user for optimal performance. The system of pads includes medial and lateral upper arm pads, medial and lateral lower arm pads, and medial and lateral hinge pads removably attached to the engagement faces of the correspondingly positioned rigid frame components. The areal dimensions and shape of the pads correspond to the areal dimensions and shape of the engagement faces, enabling the pads to fully cushion the body from the rigid frame components.

With the brace in place on the leg of a user, the size, and in particular the thickness, of the pads is systematically adjusted by inflating or deflating the pads as desired to closely the fit the brace with the specific contours of the leg of the user. The pad system also permits the user to instantaneously adapt the fit of the brace to different user activities or to changing conditions of the leg. Thus, for example, if swelling is experienced in the leg, the user can deflate predetermined pads to reduce the thickness of one or more pads and correspondingly reduce the pressure of the brace on the leg, enhancing the comfort of the user. In contrast, if undesirable movement of the brace is experienced relative to the leg during vigorous physical activity, the user can inflate one or more predetermined pads to increase the thickness thereof, increasing the pressure of the brace on the leg and providing a tighter fit of the brace to the leg.

The present invention will be further understood, both as to its structure and operation, from the accompanying drawings, taken in conjunction with the accompanying description, in which similar reference characters refer to similar parts.

DESCRIPTION OF PREFERRED EMBODIMENTS

Figures 1, 2:
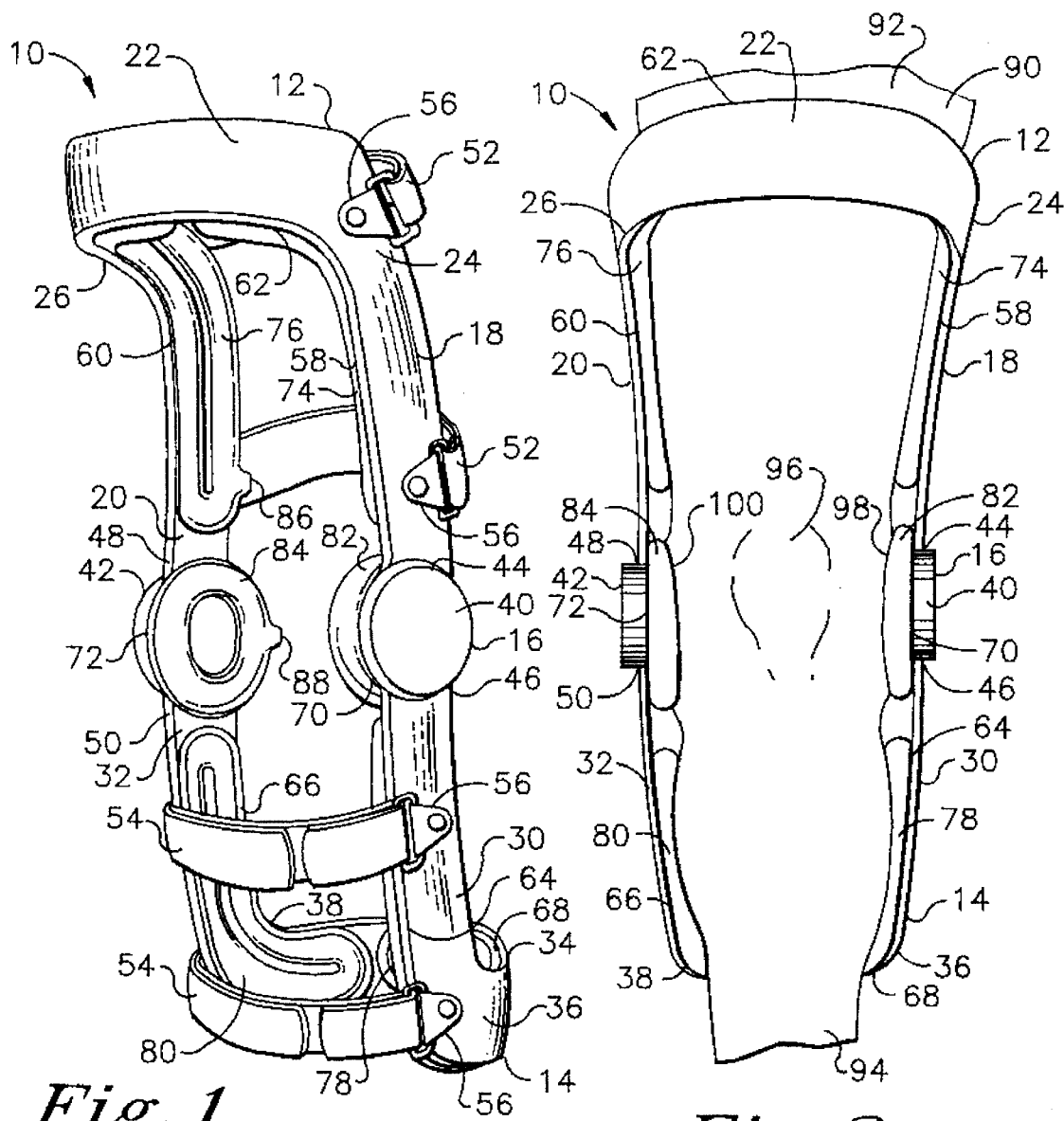
FIG. 1 is a perspective view of a knee brace of the present invention.
FIG. 2 is a frontal view of the knee brace of FIG. 1 in place on the leg of a user.

Referring initially to FIG. 1, an orthopedic brace of the present invention is shown and generally designated 10. The orthopedic brace 10 shown by way of example is a knee brace for the right leg. The brace 10 has a frame fabricated from substantially rigid components combined in a conventional design as typified by U.S. Pat. No. 4,697,583, incorporated herein by reference.

The rigid components of the frame include an upper leg cuff 12, a lower leg cuff 14, and a hinge 16. The upper leg cuff 12 comprises an upper medial arm 18 and an upper lateral arm 20 longitudinally disposed on opposite sides of the brace 10 above the hinge 16 in substantially parallel alignment with one another. An upper cross member 22 is disposed substantially perpendicular to the upper medial and lateral arms 18, 20 joining the proximal end 24 of the upper medial arm 18 opposite the hinge 16 with the corresponding proximal end 26 of the upper lateral arm 20. The upper cross member 22 has an arcuate configuration forming an anterior arc substantially in the shape of a partial circle or ellipse that conforms to the circumferential contour of the upper leg as will be shown with reference to FIG. 2.

The lower leg cuff 14 similarly comprises a lower medial arm 30 and a lower lateral arm 32 longitudinally disposed on opposite sides of the brace 10 below the hinge 16 in substantially parallel alignment with one another. A lower cross member 34 is disposed substantially perpendicular to the lower medial and lateral arms 30, 32 joining the distal end 36 of the lower medial arm 30 opposite the hinge 16 with the corresponding distal end 38 of the lower lateral arm 32. The lower cross member 34 has an arcuate configuration forming a posterior arc substantially in the shape of a partial circle or ellipse that conforms to the circumferential contour of the lower leg as will also be shown with reference to FIG. 2.

The hinge 16 comprises a medial pivot member 40 and a lateral pivot member 42 disposed on opposite sides of the brace 10 and intermediately positioned between the upper and lower leg cuffs 12, 14. The distal end 44 of the upper medial arm 18 is rotatably attached to the proximal end 46 of the lower medial arm 30 at the medial pivot member 40. The distal end 48 of the upper lateral arm 20 is correspondingly rotatably attached to the proximal end 50 of the lower lateral arm 32 at the lateral pivot member 42.

In addition to the above-described rigid frame components, the brace 10 further comprises a pair of upper straps 52 above the hinge 16 and a pair of lower straps 54 below the hinge 16 to secure the brace 10 to the leg of a user. The upper straps 52 circumscribe the posterior of the brace 10 opposite the upper cross member 22 and the lower straps 54 similarly circumscribe the anterior of the brace 10 opposite the lower cross member 34. The straps 52, 54 are attached to the frame of the brace 10 by means of loop fixtures 56.

Each of the rigid frame components has an inner surface engageable with the leg that is accordingly termed an engagement face. Thus, the upper medial arm 18 has an engagement face 58, the upper lateral arm 20 has an engagement face 60, and the upper cross member 22 has an engagement face 62. Similarly, the lower medial arm 30 has an engagement face 64, the lower lateral arm 32 has an engagement face 66, and the lower cross member 34 has an engagement face 68. Finally, the medial and lateral pivot members 40 and 42 have engagement faces 70 and 72, respectively.

The brace 10 further comprises a system of pads removably attachable to the above-recited engagement faces, thereby positionable between the rigid frame components and the leg of the user as will be shown with reference to FIG. 2. The pad system comprises a plurality of arm pads including an upper medial arm pad 74, an upper lateral arm pad 76, a lower medial arm pad 78 and a lower lateral arm pad 80. Arm pads 74, 76, 78, 80 all have a substantially identical configuration and construction as will be described hereafter with reference to FIGS. 3 and 4.

Figure 5:
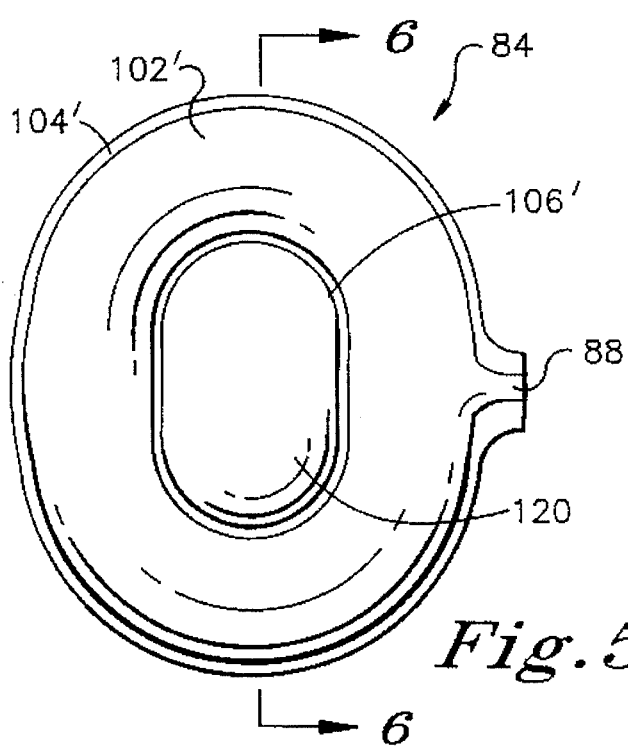
FIG. 5 is a frontal view of a hinge pad associated with the knee brace of FIG. 1.

The pad system further comprises a pair of hinge pads including a medial hinge pad 82 and a lateral hinge pad 84, both having a substantially identical configuration and construction as will be described hereafter with reference to FIGS. 5 and 6. From FIG. 1, however, it is apparent that the arm pads 74, 76, 78, 80 substantially correspond to the profile of the respective arm engagement faces 58, 60, 64, 66 and a portion of the adjoining cross member engagement faces 62, 68. The hinge pads 82, 84 likewise substantially correspond to the profile of the respective pivot member engagement faces 70, 72.

All of the pads are removably attachable to the respective engagement faces by conventional means, such as hook and loop fasteners commonly known as VELCRO (not shown in FIG. 1). The preferred fastener is a segment of the hook or loop material fixably attached to the side of a pad abutting the respective engagement face and a complementary segment of the hook or loop material fixably attached to the engagement face. A garment material, such as natural or synthetic cloth or leather, may further be affixed to the opposite side of the pad abutting the body to enhance the comfort of the user. Synthetic chamois is a preferred garment material.

Each of the arm pads 74, 76, 78, 80 and hinge pads 82, 84 is preferably alternately inflatable or deflatable by means of a selectively sealable valve as shown in FIG. 1 by representative substantially identical valves 86 and 88 that are integrally formed in the upper lateral arm pad 76 and the lateral hinge pad 84, respectively. The valve 86 permits selective fluid communication between the interior and exterior of the pad 76 with the valve 86 preferably biased in the closed position and opened by insertion of a pump needle (not shown) therein. A detachable pump or a pump integral with each valve (not shown) can be used to inflate the respective pad. Teaching of such pumps and valves is conventional and, thus, well known to those skilled in the art.

In any case, a preferred fluid for injection by means of a pump into a pad in the manner set forth above is a compressible fluid, more preferably a gas, and most preferably air at ambient atmospheric conditions. The injection of other gaseous, liquid or gel-like fluids, however, is possible within the scope of the present invention. It is further understood that the injected fluid can conversely be withdrawn from a pad by opening a valve and displacing the fluid in the pad interior through the valve to the exterior thereof.

The relative positioning of the brace 10 including the pad system is shown on the right leg 90 of a user with reference to FIG. 2. For clarity the straps 52, 54 are not shown, but it is understood that in practice the straps 52, 54 would be present and functional. FIG. 2 shows the upper leg cuff 12 engaging the upper leg 92, and specifically engaging the medial, lateral and anterior thigh region. It is further apparent from FIG. 2 that the lower leg cuff 14 engages the lower leg 94, and specifically engages the medial, lateral and posterior calf region. The arm pads 74, 76, 78, 80, which are positioned between the upper and lower leg cuffs 12, 14 and the upper and lower legs 92, 94, respectively, are shown to fit snugly therebetween, compressed flush against the relatively smooth even surfaces of the upper and lower legs 92, 94 and the respective engagement faces. In so doing, the arm pads 74, 76, 78, 80 provide a close even overall fit of the brace 10 with the leg 90.

The hinge 16 is positioned adjacent to the knee joint 96 to transfer loads between the upper and lower leg cuffs 12, 14 and to restrict flexion or extension of the knee joint 96 as desired in accordance with conventional flexion or extension restriction means, such as taught by U.S. Pat. Nos. 4,481,941 and 4,531,515. The medial and lateral pivot members 40, 42 engage the medial and lateral condyles 98, 100, respectively, of the knee joint 96. The hinge pads 82, 84 are positioned between the medial and lateral pivot members 40, 42 and the medial and lateral condyles 98, 100, respectively, to compress flush against the smooth even surfaces of the pivot member engagement faces 70 72, while conforming around the protruding condyles 98, 100. Thus, the hinge pads 82, 84 augment the arm pads 74, 76, 78, 80 in fitting the brace 10 to the leg 90.

Figure 3:
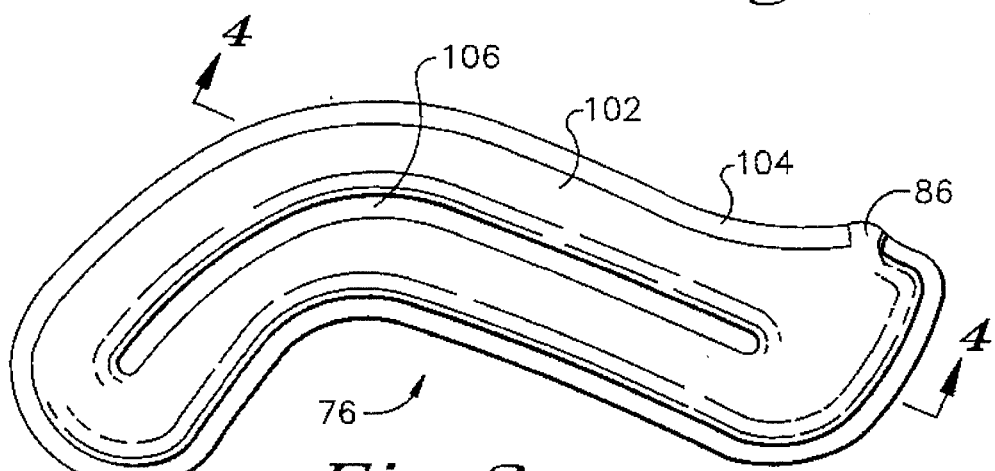
FIG. 3 is a frontal view of an arm pad associated with the knee brace of FIG. 1.

Details of the preferred configuration and construction of the arm pads 74, 76, 78, 80 are described with reference to FIGS. 3 and 4, wherein the upper lateral arm pad 76 is shown as representative of all the arm pads. The pad 76 is a fluid-retaining bladder 102 having a peripheral seam 104 that is penetrated by the valve 86 integrally positioned in the seam 104. The pad 76 also has an interior seam 106 surrounded by the bladder 102 and peripheral seam 104.

When independent of the associated upper lateral arm 20 and upper cross member 22, the free-standing pad 76 is substantially planar. However, when attached to the arm 20 and adjoining upper cross member 22 as shown in FIG. 2, the inflated pad 76 is twistable to a three-dimensional configuration conforming thereto, and substantially covering the engagement face 60 and a portion of the engagement face 62 corresponding to one quadrant of a circle defined by the cross member 22. Remaining pads 74, 78, 80 similarly conform to respective engagement faces as shown in FIG. 2.

The presence of the interior seam 106 on the pad 76 facilitates conformance of the pad 76 to the respective engagement faces 60, 62, thereby enhancing the fit of the brace 10 to the leg 90. The interior seam 106 also functions to desirably increase the contact interface between the pad 76 and the upper leg cuff 12, further enhancing the fit of the brace 10 to the upper leg 90. The interior seam 106 essentially bifurcates the substantially convex, tubular-shaped bladder 102, thereby significantly increasing the contact surface of the pad 76 relative to a similar configuration absent the interior seam 106.

Figure 4:
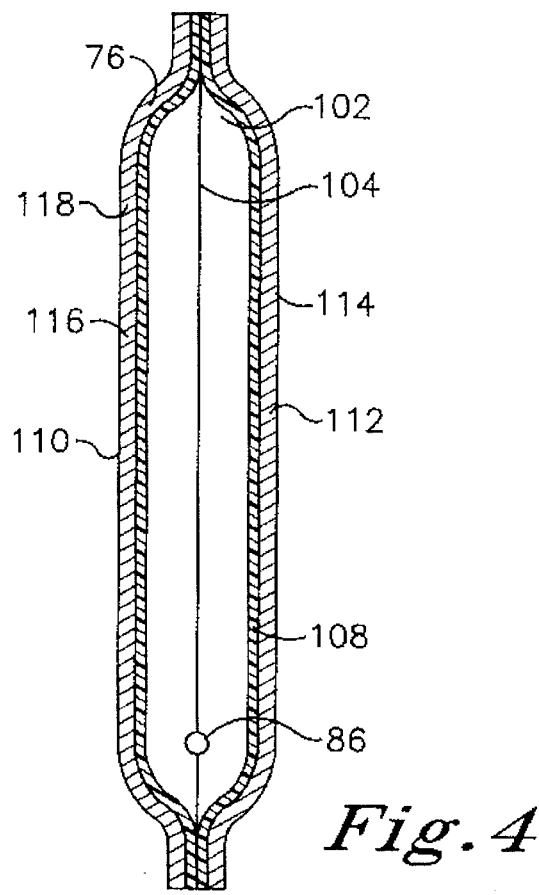
FIG. 4 is a cross-sectional view of the arm pad of FIG. 3 as seen along line 4—4.

Referring to FIG. 4, the pad 76 is shown to have a laminate construction comprising two continuous sheets 108, 110 of a fluid-impervious film material covered by a single sheet of the garment material 112 on the leg-facing side 114 of the pad 76, and a single sheet of a fastenable material 116 on the opposite brace-facing side 118 of the pad 76. The film material is a highly-flexible, elastically-collapsible material that is preferably gas-impervious, such as a plastic, e.g., polyurethane or polyvinyl chloride. The fastenable material is preferably a loop coupling of a hook and loop fastener or, alternatively, the hook coupling thereof.

The pad 76 is constructed by overlaying the first sheet 108 atop the second sheet 110 and placing the sheet of garment material 112 and the sheet of fastenable material 116 on either side of the sheets 108,110. An adhesive may be placed between sheets 108 and 112 or between sheets 110 and 116 to bond the respective sheets together. The components of the valve 86 are subsequently placed at a desired location between the sheets 108, 110 where the peripheral seam 104 is to be formed.

The peripheral seam 104 is formed by joining all of the sheets 108, 110, 112, 114 together along the continuous path of the outer perimeter of the pad 76 using conventional means, such as high radio frequency (r.f.) welding or thermal welding. The valve 86 is likewise bonded into the seam 104. The interior seam 106 is similarly formed by joining the sheets 108, 110, 112, 114 together along the predetermined interior path.

If desired, the tubular, or alternately hemi-tubular, configuration of the pad 76 can be preformed by preliminarily thermoforming both or one of the sheets 108, 110 in a hemi-tubular shape prior to joining them together. Inflation of the pad 76, however, is generally sufficient to establish the tubular configuration thereof without the preforming step.

Details of the preferred configuration and construction of the hinge pads 82, 84 are described with reference to FIGS. 5 and 6, wherein the lateral hinge pad 84 is shown as representative of both hinge pads. Like the arm pad 76, the hinge pad 84 is a fluid-retaining convex bladder 102' enclosed by a peripheral seam 104' that is penetrated by the valve 88 integrally positioned in the seam 104'. An interior seam 106' is likewise provided that is surrounded by the bladder 102' and the peripheral seam 104'.

The pad 84 has a substantially planar configuration whether free-standing independent of the associated pivot member 42 or attached thereto. The pad 84 effectively covers the engagement face 72 when attached thereto. The remaining pad 82 similarly conforms to the engagement face 70 as shown in FIG. 2.

The presence of the interior seam 106' on the pad 84 facilitates conformance of the pad 84 to the protruding condyle 100, thereby enhancing the fit of the brace 10 to the leg 90. The interior seam 106' provides the bladder 102' with a substantially convex toroidal shape that is bounded on the outer perimeter by the seam 104' and bounded on the inner perimeter by the seam 106'.

Figure 6:
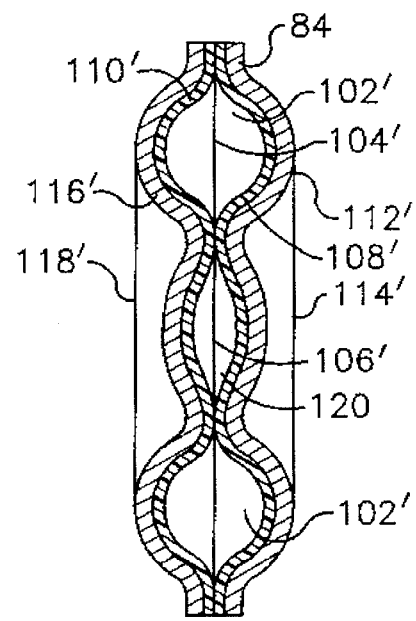
FIG. 6 is a cross-sectional view of the arm pad of FIG. 5 as seen along line 6—6.

Referring to FIG. 6, the pad 84, like pad 76, is shown to have a laminate construction comprising sheets 108', 110', 112', 116' similar to sheets 108,110,112,116, respectively. It is apparent that the sheets of the pad 84 are combined in substantially the same manner as pad 76. However, a second bladder 120 arealy interior to bladder 102' may additionally be provided in the pad 84 by maintaining the fluid-impervious integrity of the sheets 108', 110' interior to the seam 106'.

The interior bladder 120 can be in fluid isolation from the bladder 102' and can be evacuated or have a fluid, such as air, sealed therein during the fabrication process. In yet another alternative not shown, the bladder 120 can be in fluid communication with the bladder 102' by means of gaps provided in the seam 106' thereby rendering the bladder 120 simultaneously inflatable with the bladder 102'.

In any case, where a second bladder 120 is provided interior to the bladder 102', the bladders 102' and 120 are constructed such that the bladder 102' always maintains a greater elevation than the bladder 120 when the bladder 102' is inflated. Thus, the distance separating sheets 108', 110' within the bladder 102' is substantially greater than the distance of separation within the second bladder 120. This characteristic enables the pad 84 to receive the protrusion of the condyle 100 within the interior of the bladder 102', thereby substantially securing the brace 10 about the knee joint 96 while enhancing the comfort of the user.

Although preferred embodiments of the arm pad 76 and the hinge pad 84 have been shown and described above, it is apparent that other embodiments of the pads, although not shown, are possible within the scope of the present invention. For example, the present invention provides for an alternate embodiment of a hinge pad having only a single primary bladder similar in configuration to the bladder 102' of FIG. 5. Unlike the pad 84 of FIG. 5, however, the second bladder is excluded from the central opening of the toroidal-shaped bladder so that the opening is maintained as a void.

Further within the scope of the present invention, it is understood that the bladder of the hinge pad need not have a continuous toroidal shape, but may have substantially any shape defining a closed-loop or open-loop pathway that conforms to the perimeter of a condyle and that provides an interior opening for receiving the condyle. It is desirable that the bladder is sufficiently inflated to maintain the thickness of the bladder greater than the height of the protruding condyle received therein during use of the brace to prevent substantial compressive contact of the condyle with the rigid hinge.

Alternative means for producing the pads of the present invention are also provided within the scope of the invention. For example, the pads can be formed from a single sheet of film material, rather than two sheets as disclosed above, by joining the edges of a single sheet together and welding the resulting joint, thus, forming a bladder sealed at the weld or welds. In other production alternatives, the pad may be formed by blow molding or other conventional molding methods available to one skilled in the art.

Also encompassed within the present invention is a method for initially fitting the brace 10 to the body of a user, or subsequently modifying the fit of the brace 10 in response to different activities performed by the user, or in response to variations in the condition of the body part adjacent to the brace 10. The method comprises individually controlling the size, and in particular the thickness, of each pad by systematically injecting or withdrawing fluid through the valve, i.e., inflating or deflating the pad, in accordance with the specific needs of the user. Thus, for example, if the initial fit of the brace 10 is too loose about the upper leg 92, upper arm pads 74, 76 can be inflated, increasing their thickness until a snug fit is achieved. If maximum inflation of the pad is reached without achieving a proper fit, the pad can be removed and replaced with a pad having a larger capacity. By providing a matrix of pads with different inflation capacities, a virtually custom fit of the brace can be assured.

If the brace 10 is initially fitted correctly on the leg, but the leg subsequently swells due to activity or treatment, the pressure of the leg against the brace can be relieved by systematically withdrawing fluid from the pads, reducing their thickness until an acceptable degree of comfort is achieved. Conversely, if swelling of the leg subsequently diminishes due to healing, the pressure of the leg against the brace can be increased by systematically injecting fluid into the pads, increasing their thickness. In yet another application of the present method, the degree of inflation, and correspondingly the thickness, of the pads can be systematically increased to desirably tighten the fit of the brace and prevent slippage in anticipation of vigorous activity. Conversely, the degree of inflation, and correspondingly the thickness, of the pads can be systematically decreased to desirably loosen the fit of the brace in anticipation of relaxation.

While the forgoing preferred embodiments of the invention have been described and shown, it is understood that alternatives and modifications, such as those suggested and others, may be made thereto and fall within the scope of the invention.

We claim:

1. A knee brace positionable on a leg comprising:

an upper leg cuff having an upper inside face positionable adjacent to the upper leg;

a lower leg cuff having a lower inside face positionable adjacent to the lower leg;

a hinge rotatably connecting said upper leg cuff and said lower leg cuff, wherein said hinge has an intermediate inside face positionable adjacent to the knee joint; and a pad positioned on said intermediate inside face having a fluid-retaining bladder and a selectively sealable valve penetrating said bladder enabling injection of fluid into or withdrawal of fluid from said bladder, wherein said pad has a loop pathway defining an interior opening, said pathway having a size adaptable to circumscribe a knee condyle and said opening having a size adaptable to receive the knee condyle.

2. A pad as recited in claim 1 wherein said loop pathway is a closed loop.

3. A pad as recited in claim 1 wherein said loop pathway is an open loop.

4. A knee brace positionable on a leg comprising:

an upper leg cuff having an upper inside face positionable adjacent to the upper leg;

a lower leg cuff having a lower inside face positionable adjacent to the lower leg;

a hinge rotatably connecting said upper leg cuff and said lower leg cuff, wherein said hinge has an intermediate inside face positionable adjacent to the knee joint; and a pad positioned on said upper inside face or said lower inside face having a fluid-retaining bladder and a selectively sealable valve penetrating said bladder enabling injection of fluid into or withdrawal of fluid from said bladder, wherein said pad has an elongate configuration with a longitudinal axis and a substantially right angle bend formed therein to align said pad with said upper or lower inside face.

5. A knee brace as recited in claim 4, wherein said pad has an interior seam dividing said bladder and, wherein said interior seam is substantially aligned with the longitudinal axis of said pad.

* * * * *